United States Patent
Netzer

[11] Patent Number: 5,751,071
[45] Date of Patent: May 12, 1998

[54] WINDOW CAPACITIVE MOISTURE SENSOR

[76] Inventor: Yishay Netzer, Yuvalim, Doar Na Misgav, Israel

[21] Appl. No.: 625,473

[22] Filed: Mar. 29, 1996

[51] Int. Cl.$^6$ ............................................. H05B 1/02
[52] U.S. Cl. ...................... 307/10.1; 52/171.2; 219/203
[58] Field of Search ........................ 307/9.1, 10.1, 307/118, 141.4; 219/202, 203, 522; 52/171.2; 318/483; 361/286, 181; 340/602

[56] References Cited

U.S. PATENT DOCUMENTS

| | | | |
|---|---|---|---|
| 4,032,745 | 6/1977 | Roselli | 219/203 |
| 4,196,338 | 4/1980 | Edel | 219/203 |
| 4,520,258 | 5/1985 | Grohmann | 219/203 |
| 4,805,070 | 2/1989 | Koontz et al. | 361/286 |

*Primary Examiner*—Richard T. Elms
*Attorney, Agent, or Firm*—Mark M. Friedman

[57] ABSTRACT

An apparatus for sensing condensed moisture on the inside of automotive windows with essentially no sensitivity to precipitation on the outside of the window. The apparatus senses the influence of the moisture on the impedance (mainly capacitive) between two electrodes. It is intended especially for rear windows where the sensing electrodes can be integrated with the resistive heater network printed on the internal side and activate it automatically. Similarly it can be used for front windows where it can automate the operation of electrical or hot-air defoggers.

11 Claims, 4 Drawing Sheets

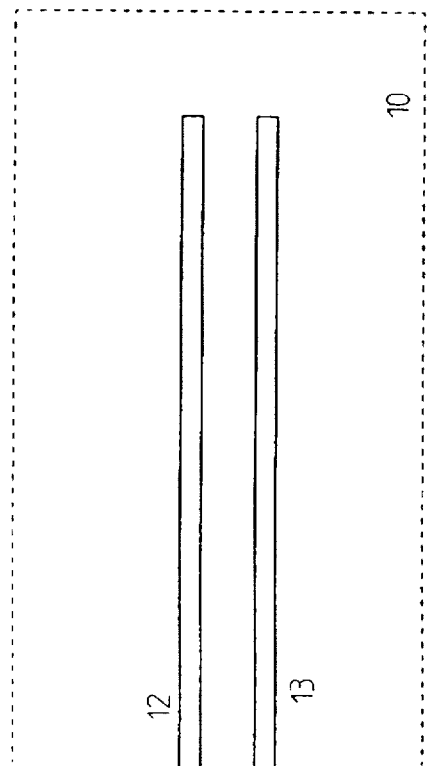
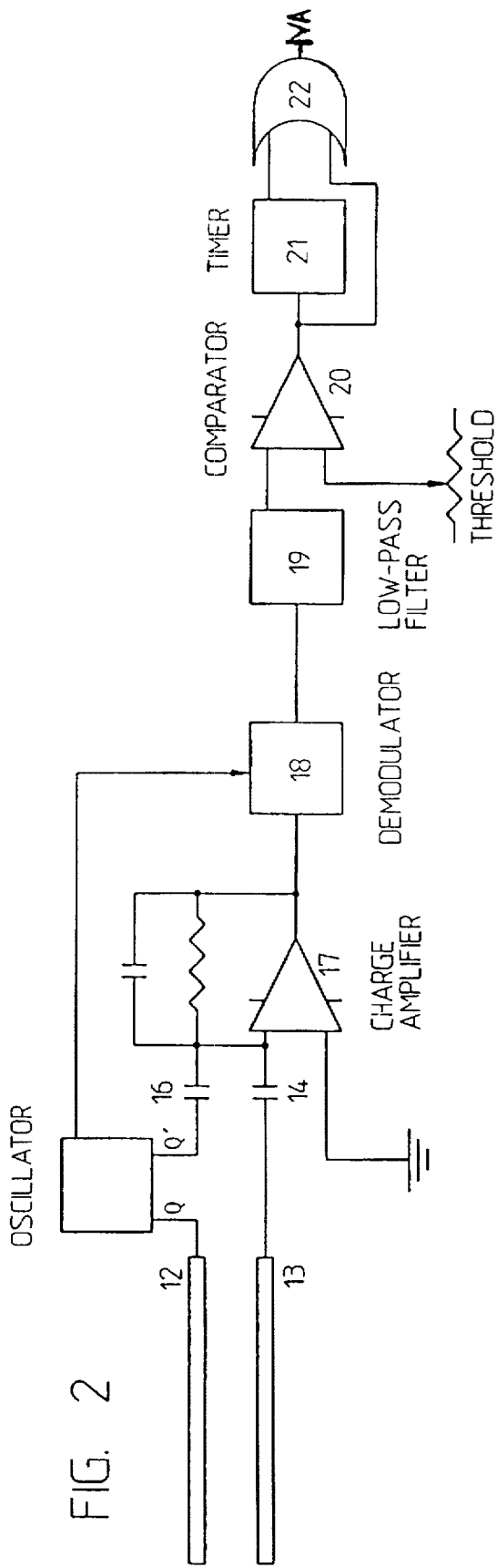
FIG. 1
FIG. 2

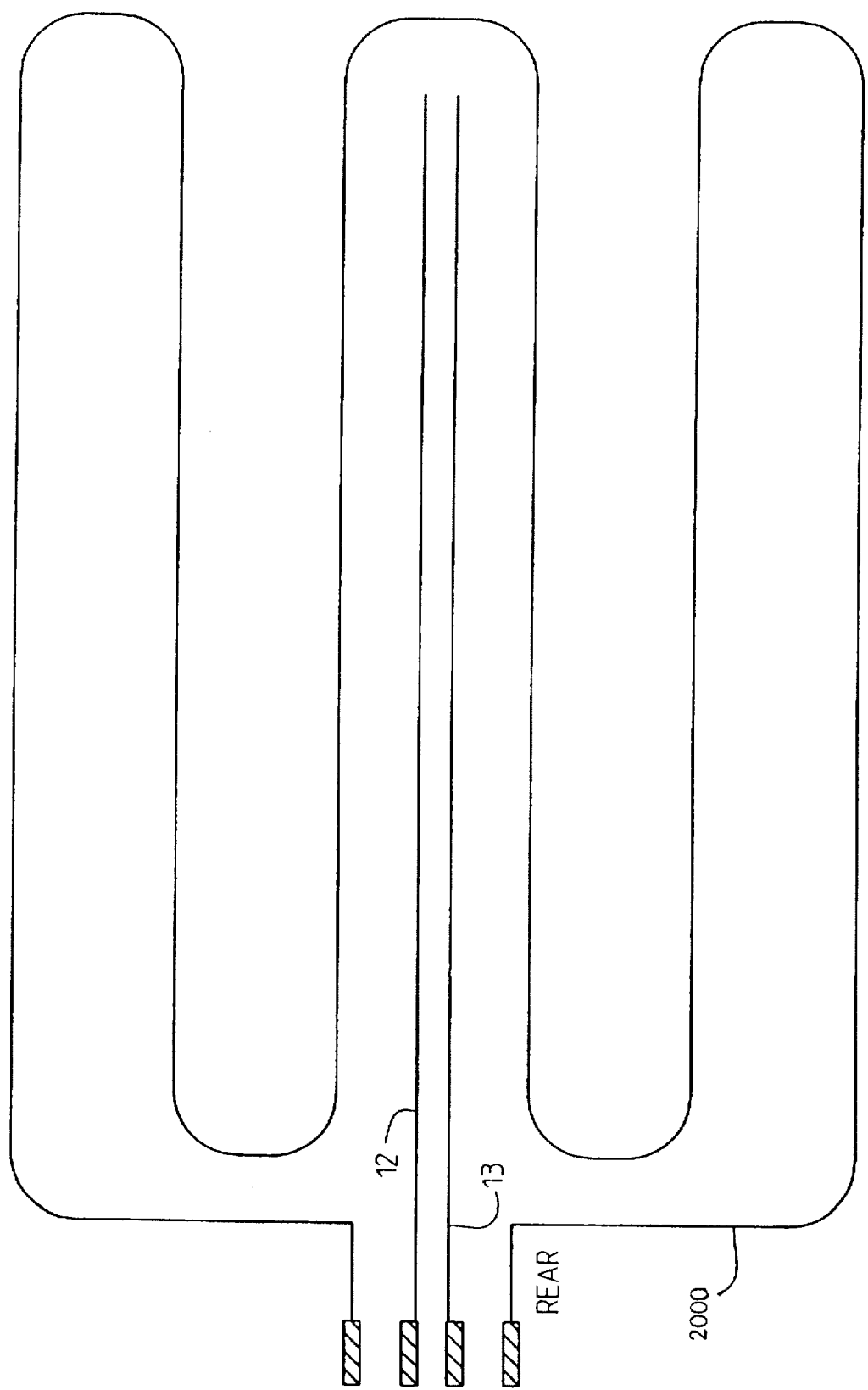

WINDOW CAPACITIVE MOISTURE SENSOR

FIELD AND BACKGROUND OF THE INVENTION

The present invention relates to automotive window moisture sensors and, more particularly, to a moisture sensor especially suitable for sensing moisture on the inner surface of automobile windows, and for automatic activation of window heaters.

Automotive windshield moisture sensors have been introduced for automating the operation of windshield wipers. One such type of moisture sensor is based on electro-optical detection of raindrops by sensing changes in the total internal reflection of a light beam reflected off the front glass-air interface. A typical moisture sensor of this type is described in U.S. Pat. No. 4,859,867.

An alternative method of sensing moisture on the windshield surface relies on the relatively large dielectric constant ((~80) of water as it affects the capacitance between a set of conductive electrodes deposited on the windshield. Moisture sensors based on this method are integral with the windshield and are potentially less expensive and less conspicuous than optical moisture sensors. Two such moisture sensors are described in U.S. Pat. Nos. 4,805,070 and 4,831,493, in which the electrodes are coated on the outside surface of the windshield, leaving the electrodes exposed to abrasion by the combined effect of the wiper motion and airborne particles.

In an attempt to overcome this weakness it was suggested that the conductive electrodes be deposited between the glass laminates of the windshield. Typical moisture sensors of this type are described in U.S. Pat. No. 3,826,979, U.S. Pat. No. 4,703,237, in U.S. Pat. No. 4,827,198, and in U.S. Pat. No. 4,554,493. However, the dielectric glass layer that separates the sensing electrodes from the water droplets decreases the moisture signal to such an extent that the moisture signal is very small compared to parasitic signals that result from temperature effects and mechanical stresses in the glass. If these parasitic signals were constant, they would result in a fixed offset sensor output error. Since the dielectric constant of the glass is temperature dependent, for example, resulting in a varying offset error, the parasitic effects should be suppressed as much as possible.

An additional shortcoming of prior art capacitive moisture sensors is their sensitivity to moisture on both sides of the windshield, i.e., they do not distinguish between moisture on the external surface of the windshield and moisture on the internal surface of the windshield.

The fact that prior art capacitive windshield moisture sensing failed to provide a viable solution to sensing moisture on the outer surface of the windshield is probably one of the reasons why capacitive moisture sensors were not even considered for other applications, such as sensing moisture on the internal surface of automotive windows for automating the operation of window heaters and hot-air defoggers. In this application the sensor would be safe from windshield abrasion, and its sensitivity would not have to be compromised by burying the electrodes between the window layers.

It is an object of the invention to provide a capacitance-type moisture sensor suitable for sensing moisture on the inner surface of an automobile window.

It is another object of the invention to provide a capacitance type moisture sensor that can be applied simultaneously in the same process with the window resistive heater network.

It is a further object of the invention to provide a window capacitive moisture sensor which is insensitive to the presence of moisture on the other, unsensed, second side of the window.

It is a further object of the invention to provide a capacitive moisture sensor for automatically activating window heaters or defoggers.

SUMMARY OF THE INVENTION

The invention provides an automotive window-moisture capacitive sensor with sensing electrodes on the internal side of the window which is substantially insensitive to precipitation on the outside of the window. The sensor is intended for rear windows. The sensing electrodes can be integrated with the window heater network, and can automatically activate the window heater network through a control circuit.

The inner surface moisture sensor of the present invention can also be applied to other windows such as front windshields, where it can automate defogging by means of hot air or electrical heating.

The sensor of the present invention is applied to the window surface on which moisture is to be detected. Thus, there is no sensitivity problem, as in the prior art sensors, since being exposed on the surface of the window, the moisture signal level is orders of magnitude greater than in the buried electrode case. Thus, the time-varying, temperature-varying, stress-dependent parasitic coupling through the glass dielectric is insignificant. Further, due to the high signal levels, there is no problem of parasitic capacitance, and no need for differential-input electronics or other precautions, like shielding. The charge amplifier, 17, should be conveniently located somewhere nearby on the edge of the window, where it will provide substantially no obscuration of the driver's field of view, and the rest of the signal processing electronics may be located in the same small module.

BRIEF DESCRIPTION OF THE DRAWINGS

The invention is herein described, by way of example only, with reference to the accompanying drawings, wherein:

FIG. 1 is a top view of a typical capacitive sensor.

FIG. 2 illustrates a typical block diagram of the moisture sensor system.

FIG. 4 illustrates an integrated sensor and heater.

DETAILED DESCRIPTION OF THE PREFERRED EMBODIMENTS

Figure 3A:
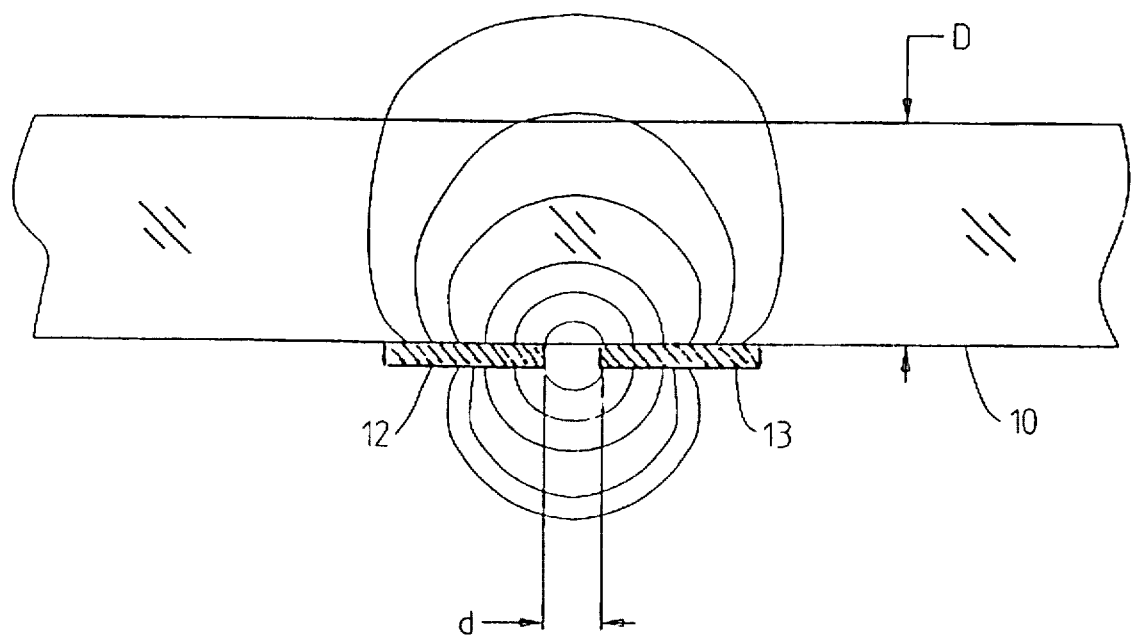
FIG. 3A is a side view of the moisture sensor.

FIG. 1 illustrates a schematic top view of a typical moisture sensor according to the present invention. The moisture sensor includes two electrodes, 12 and 13. Electrode 12 is excited by an alternating voltage source, 15, with a typical frequency of 10 kHz. The electrodes are coated on the window, 10. The electrodes may be made from any conductive material, such as vacuum deposited thin film, a silk-screen printed thick film, etc.. Electrode, 13, the signal electrode, collects the capacitively induced current as determined by the geometry of the electrodes and the medium around them, wherein the medium includes the glass window, 10, air, and, possibly, a moisture layer.

FIG. 2 illustrates a typical block diagram of the moisture sensor system. Oscillator 15 generates two complementary alternating voltages, Q and Q'. Voltage Q is applied to the excitation electrode, 12, and voltage Q' is applied to a fixed capacitor, 16, whose value nominally equals the capacitance, $C_{sensor}$, between electrodes 12 and 13 in their "dry" condition. When the electrodes are wet, the capacitance, $C_{sensor}$, increases due to the dielectric nature of water. In practice, the water may not pure because of soil, salt spray, etc. and the impedance between the electrodes may include a resistive component which, combined with any DC component of the excitation voltage, could overload the amplifier. For this reason electrode 13 is coupled to the amplifier input through coupling capacitor 14. Since capacitor 16 nominally equals $C_{sensor}$, the net current flowing into the virtual ground input of the charge-amplifier, 17, as well as the amplifier output voltage, are zero. In practice, due to manufacturing tolerances, there may be some fixed output signal even in the dry condition. This fixed output signal may be eliminated by a calibration during manufacturing.

The rest of the signal conditioning of the moisture sensor is as follows:

Demodulator 18 converts the alternating output signal of charge amplifier 17 into a unipolar voltage that is smoothed and converted into a DC voltage by low-pass filter 19. The operation of the demodulator is conventional and is based on switching its gain from −1 to +1 synchronously with excitation source 15. The output of low-pass filter 19, which depends on the thickness of the moisture layer, is compared by comparator 20, to a preset threshold voltage to generate a logic level output. The logic level output may serve as the command signal to the window heater, or defroster system. To guarantee stable transitions comparator 20 preferably includes a specific amount of hysteresis. The sensor system also includes a timer, 21, the purpose of which is explained below.

Theoretically, the sensor, as shown in FIG. 1, would be sensitive to moisture on both sides of the glass window, 10, since rain drops on the second (external) side of the window will affect the sensor capacitance as well as moisture on the active side (internal to the vehicle). Such sensitivity is undesirable, but it was found that there is a way to control it, to make it insignificantly small. This is based on the fact that the lateral separation, d, between electrodes 12 and 13 affects both the desired sensitivity to moisture on the internal side of the window and the undesirable sensitivity to water on the external side. The sensitivity to moisture on the internal side of the window is proportional to the field intensity between the electrodes, i.e., it is roughly proportional to 1/d as illustrated in the cut-away view in FIG. 3A. The sensitivity to moisture on the external side of the window depends on fringing field lines at a distance, D, from the electrodes, which is roughly proportional to d/D. The density of these lines of force is further diminished by the shunting effect of the (dielectric) glass. The ratio of the two sensitivities is therefore proportional to $D/d^2$, i.e., inversely proportional to the square of the separation, d. It was found that this ratio is about 1/20 for D=5 mm and d=1 mm. The width of the electrodes is relatively unimportant in determining the sensitivity to moisture on the unsensed surface of the window.

Figure 3B:
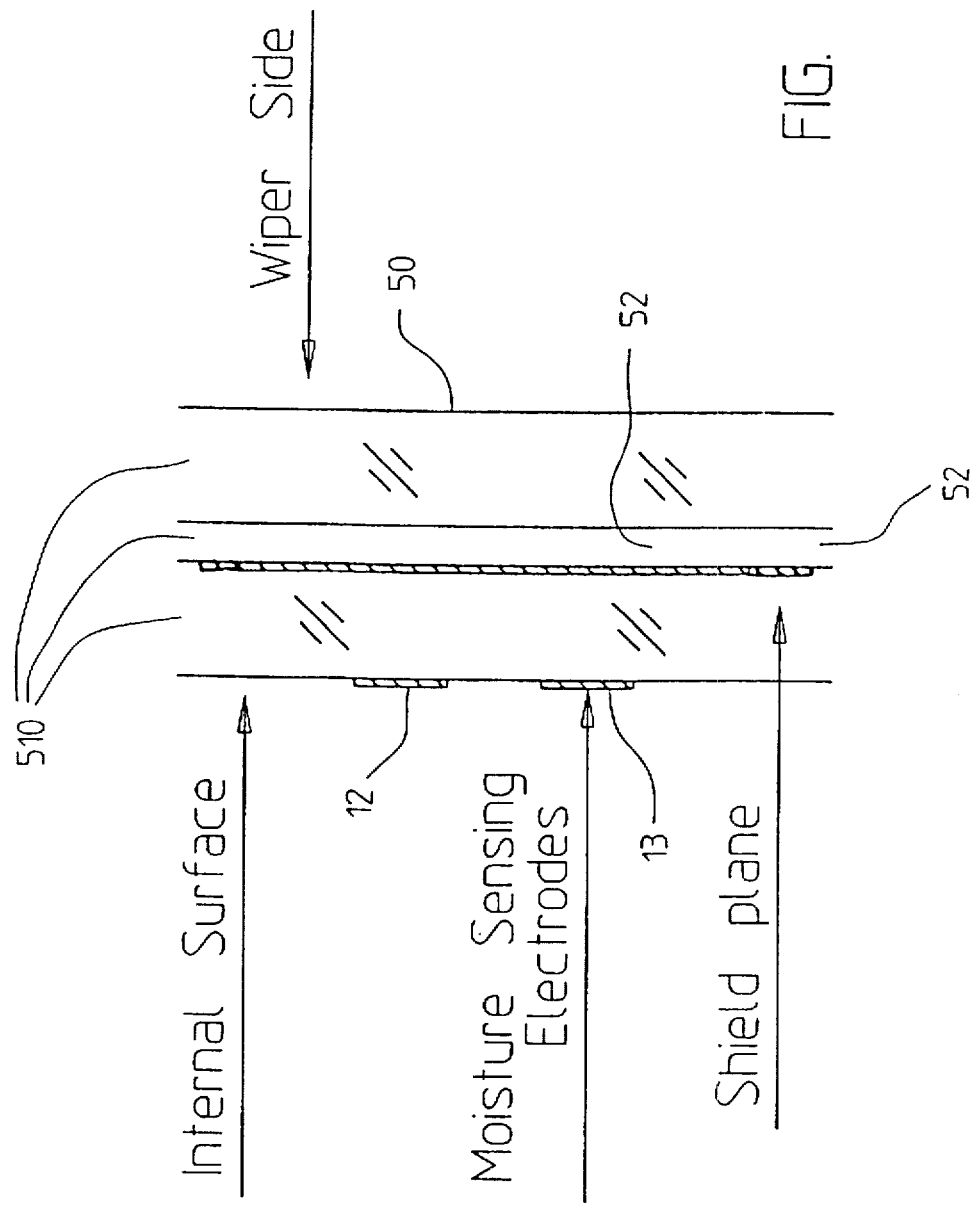
FIG. 3B is a side view of the moisture sensor with a shield layer.

In another variation, shown in FIG. 3B, a shield electrode, 51, may be incorporated on a surface the internal laminate layer, 52, of laminated automobile window sandwich glass, 510, to provide complete insensitivity to moisture on the unsensed surface, 50, of the window.

FIG. 4 illustrates a typical integrated heater network and sensor, including a patterned heater element, 2000, and two sensor electrodes, 12 and 13. The two sensor electrodes are parallel to the adjacent heater lines, and equally distant from the adjacent heater lines. The reason for this is that in the presence of moisture on the internal side of the window, the heater first evaporates the moisture near the heater lines, while the areas last to be dried are in the shape of lines parallel and between the heater lines. If the sensing electrodes are situated in this area they will sense the presence of the remaining moisture until the evaporation is complete. To assure complete evaporation, it is desirable that the heater remain on for a certain amount of time after comparator 20 switches to the low state. The low state indicates the absence of moisture. This is achieved by timer 21, which is activated by the transition of comparator 20 to the low state. Combining the comparator and timer outputs with an OR-gate 22 provides a heating command with an extra duration that guarantees a complete drying. The extra duration is the time delay provided by the time-out of timer 21, providing a heater turn-off delay.

It would be obvious to those skilled in the art that the number of electrodes as well as their geometry can be changed within the scope of the invention.

Further, the inner-surface window-moisture sensor of the present invention may be combined with other moisture sensors, to provide a complete moisture-sensing system. For example, the inner surface moisture sensor of the present invention may also be used in conjunction with prior art moisture sensors, such as the optical moisture sensors described above.

Also, the sensor electronics may be modified as necessary to suit various applications.

While the invention has been described with respect to a limited number of embodiments, it will be appreciated that many variations, modifications, and other applications of the invention may be made.

What is claimed is:

1. An capacitive moisture sensor for sensing moisture on a surface of a dielectric, which capacitive moisture sensor is insensitive to the presence of moisture on the other unsensed side of the dielectric, the capacitive moisture sensor comprising (a) at least one pair of capacitive electrode plates coated on the surface of the dielectric on which moisture is to be sensed, said at least one pair of capacitive electrode plates including at least one excitation and one signal capacitive electrode plates;

(b) electronic circuitry for substantially ignoring a resistive component of impedance between said electrode plates.

2. A moisture sensor as in claim 1, wherein the moisture sensor is made insensitive to moisture on the other unsensed side of the dielectric by controlling the lateral separation between said sensor electrodes.

3. A moisture sensor as in claim 2, said capacitive electrodes having a lateral separation, d, wherein said moisture sensor is made insensitive to moisture on the other unsensed side of the dielectric, the dielectric having a thickness D, by controlling the ratio, $D/d^2$, of said thickness, D, of the dielectric, to $d^2$, the square of said lateral separation, d, between said capacitive electrodes.

4. A moisture sensor as in claim 3, further comprising a heater and sensor electronics circuitry to activate said heater when moisture is sensed, said electronics circuitry including a turn-off delay to assure complete evaporation of moisture on the sensed surface.

5. A moisture sensor as in claim 2 applied on the inside of the front window in a motor vehicle for automating the operation of a window defogger/heater.

6. A moisture sensor as in claim 2 applied on the inside of the rear window in motor vehicle for automating the operation of a window heater.

7. A moisture sensor as in claim 1, wherein the dielectric is sandwich glass having an internal laminate layer, said moisture sensor insensitive to moisture on the other unsensed side of the dielectric including an electrically conductive shield layer on a surface of said internal laminate layer of said sandwich glass.

8. A capacitive moisture sensor as in claim 1, having excitation and signal capacitive electrode plates, further comprising (a) an alternating excitation source connected to the excitation capacitive electrode plate;

(b) the signal electrode plate for collecting capacitively induced signal connected to an amplifier which provides an amplified capacitively induced signal; and, (c) a synchronous demodulator coupled to the signal electrode plate for synchronously demodulating said amplified capacitively induced signal synchronously with said alternating excitation source.

9. A capacitive moisture sensor as in claim 8, having a sensitivity to moisture on the surface of the window on which moisture is to be sensed, the window having a thickness, D, further comprising separating said excitation and signal capacitive electrode plates by a distance, d, thereby resulting in a fringing field on the other unsensed side of the window roughly proportional to d/D, thereby resulting in a ratio of said sensitivity to moisture on the surface of the window on which moisture is to be sensed, to said sensitivity to moisture on the other unsensed side of the window, roughly proportional to $D/d^2$.

10. A capacitive moisture sensor as in clam 1, wherein said electronic circuitry for substantially ignoring a resistive component of impedance between said electrode plates includes a synchronous demodulator.

11. A window moisture sensing and evaporating system including an capacitive moisture sensor for sensing moisture on a surface of a window, which moisture sensor is insensitive to the presence of moisture on the other unsensed side of the window, comprising (a) an electrical heater element on a window surface; and, (b) the moisture sensor including at least two capacitive electrodes, including at least one each excitation and signal capacitive electrode plates, on the surface of the window on which moisture is to be sensed, the moisture sensor for use for the control of said electrical heater element.

* * * * *